United States Patent [19]

Daily

[11] 4,154,245
[45] May 15, 1979

[54] APPARATUS FOR LOCAL HYPOTHERMIA

[76] Inventor: Pat O. Daily, 7070 Fairway Rd., La Jolla, Calif. 92037

[21] Appl. No.: 814,407

[22] Filed: Jul. 11, 1977

[51] Int. Cl.² .............................................. A61F 7/00
[52] U.S. Cl. .................................. 128/400; 128/401; 128/402
[58] Field of Search .............................. 128/399–403, 128/24.1, 254, 258

[56] References Cited

U.S. PATENT DOCUMENTS

| 267,435 | 11/1882 | Leiter | 128/402 |
|---|---|---|---|
| 500,568 | 7/1893 | Ells | 128/402 |
| 1,777,982 | 10/1930 | Popp | 128/402 |
| 2,250,325 | 7/1941 | Barnes | 257/12 |
| 2,726,658 | 12/1955 | Chessey | 128/400 |
| 3,091,242 | 5/1963 | Johnson et al. | 128/402 |
| 3,170,465 | 2/1965 | Henney et al. | 128/401 |
| 3,238,944 | 3/1966 | Hirschhorn | 128/400 |
| 3,293,868 | 12/1966 | Gonzalez | 62/3 |
| 3,485,245 | 12/1969 | Lahr et al. | 128/272 |
| 3,717,199 | 2/1973 | Dienst | 165/46 |
| 3,736,769 | 6/1973 | Petersen | 128/402 |
| 3,738,372 | 6/1973 | Shioshirli | 128/400 |
| 3,830,676 | 8/1974 | Elkins | 156/289 |

Primary Examiner—Lawrence W. Trapp
Attorney, Agent, or Firm—Brown & Martin

[57] ABSTRACT

A pad for cooling the heart or other similar organs during surgery comprises a pad of a generally flat configuration constructed of a pliable material having heat transfer means in the form of a conduit for conducting a coolant through the pad adjacent one surface and an insulating device in the form of an air chamber insulating the cooling apparatus from the opposite face of the pad and including a malleable frame within the pad for maintaining the pad in selected configurations for folding around an organ, and retaining the pad in position.

9 Claims, 4 Drawing Figures

APPARATUS FOR LOCAL HYPOTHERMIA

BACKGROUND OF THE INVENTION

The present invention relates to surgical apparatus and pertains particularly to apparatus for cooling organs during surgery.

It is desirable at times to either heat or cool portions of the human body for either changing or maintaining the portion at a particular temperature. For example, the body or portions of the body are sometimes cooled during surgery. This reduces the oxygen requirements of the body portion during surgery. Local hypothermia is known in the art and many devices for the application of local hypothermia are known. However, most such devices are bulky and inconvenient to use. Many such devices are also complicated and require the enclosure and attendant fastening and unfastening of the apparatus which takes time and complicates procedures.

It is desirable that some simple and convenient device be available which can be used to quickly and conveniently enclose substantial portions of an organ such as a heart during surgery and to insulate it from other portions of the body.

SUMMARY AND OBJECTS OF THE INVENTION

It is the primary object of the present invention to overcome the above problems of the prior art.

Another object of the present invention is to provide a thermal pad which is quickly and conveniently applicable to at least partially encircle a portion of the anatomy for the application of a temperature controlling medium thereto.

A further object of the present invention is to provide a simple, convenient, and inexpensive device for local hypothermia.

In accordance with the primary aspect of the present invention, a device for controlling the temperature of a portion of the body comprises a generally flat pad constructed of a pliable material having heat transfer means disposed therein and including malleable structure for maintaining the pad in any desired fixed configuration.

BRIEF DESCRIPTION OF THE DRAWING

The above and other objects and advantages of the present invention will become apparent from the following description when read in conjunction with the drawing, wherein.

DETAILED DESCRIPTION OF A PREFERRED EMBODIMENT

Figure 1:
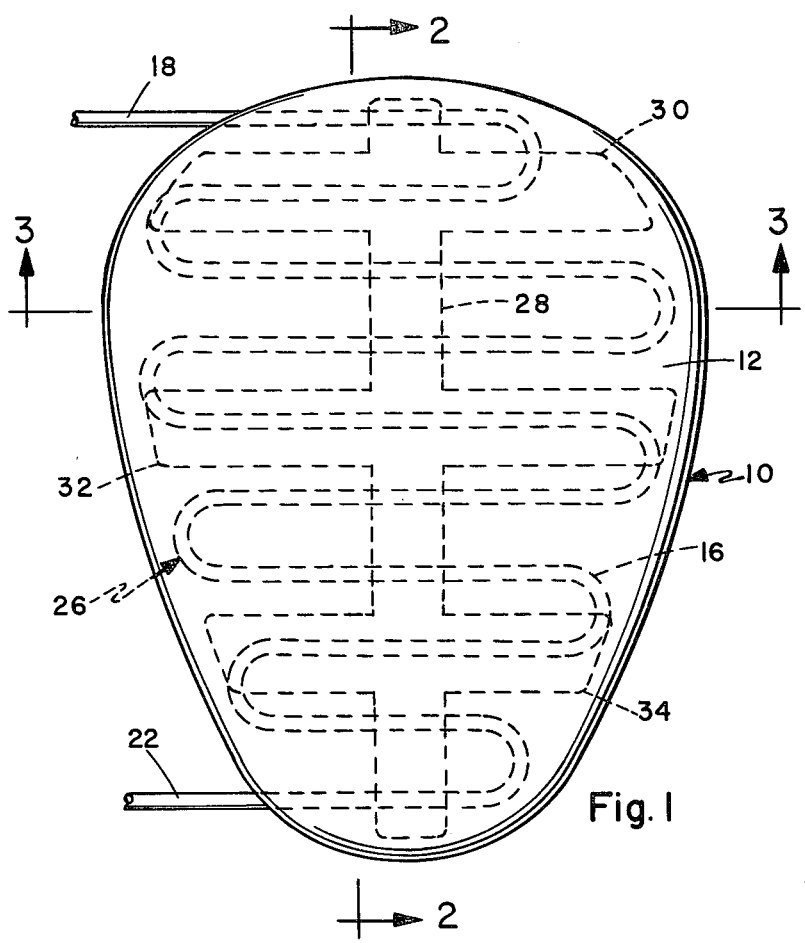
FIG. 1 is a top plan view of the pad.
Figure 2:
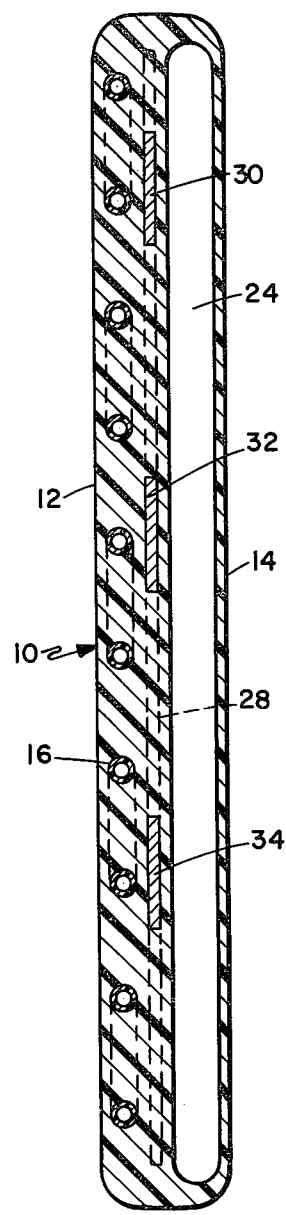
FIG. 2 is an enlarged sectional view taken on line 2—2 of FIG. 1.

Turning now to the drawing, there is illustrated a pad in accordance with the present invention. The pad, designated generally by the numeral 10, comprises a body of a generally flat configuration having a cooling face 12 and an insulating face 14. The pad has a generally flat configuration with the cooling face 12 and the insulating face 14 extending generally parallel and defined by generally flat planes in the normal configuration. The body is constructed of a suitable pliable material, such as a sterilizable plastic. The material from which the pad is constructed can be any suitable form of water proof sterilizable material, such as rubber, synthetic rubber, or any other form of suitable elastomeric material. In order to be sterilizable, the material must be able to withstand sufficient heat and/or the necessary sterilizing fluid or chemical.

The pad is provided with heat transfer means in the form of a circuitous passageway 16 which may be in the form of a tube, interconnected cells, or a passageway molded into the heat exchange side of the pad closely adjacent the cooling surface 12. The passage 16 includes an inlet conduit 18 for connection to a suitable source of heat transfer fluid and an outlet line 22 for return of the fluid to the heat or cooling source.

Suitable insulating means in the form, for example, of an air cavity or chamber 24 is formed between the heat transfer means and the face 14. Other forms of insulation may be utilized, however the air cavity as disclosed is simple and effective.

The pad is provided with a suitable malleable frame 26 molded into the body of material making up the pad. This malleable frame, as shown, includes a central sheet metal spine 28 and a plurality of cross bars 30 through 34 defining arms extending outward therefrom. This framework may be any suitable malleable metal which holds the pad in a formed configuration as shown for example, in FIG. 4.

Figure 4:
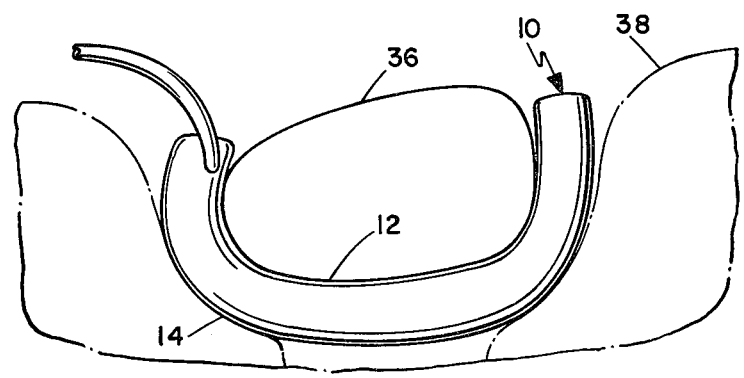
FIG. 4 illustrates the pad fitted around an organ in a body cavity.
Figure 3:
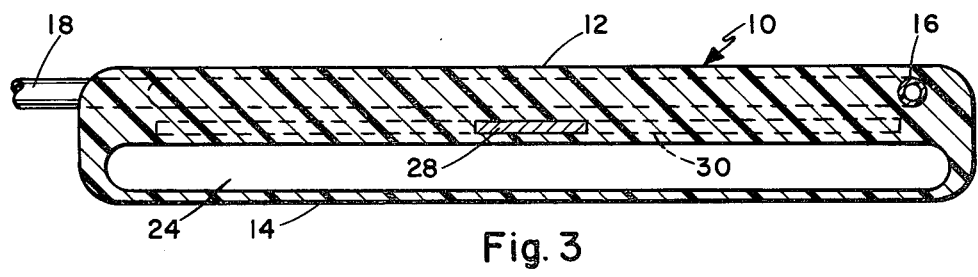
FIG. 3 is an enlarged sectional view taken on line 3—3 of FIG. 1.

In use of the device for open heart surgery, for example, the device is placed around the heart in the chest cavity in most procedures. In the case of heart transplantation, a heart 36 of a patient is removed from the body and placed on the cooling surface 12 of the pad which is then formed around or shaped around the heart, as illustrated in FIG. 4, to at least partially encase the heart. The heart is then supported on the pad which is supported on or in the cavity of the body 38 as shown in FIG. 4. The cooling surface or face 12 of the pad is in direct contact with the heart 36 and the insulating face 14 is in contact with the remainder of the body. In this manner the heart or organ which is being operated on is isolated and cooled without affecting the remainder of the body.

The insulation chamber 24 prevents the transfer of heat from the remainder of the body to the heart or organ being operated on. The malleable rib or frame structure permits the quick and effective encirculation or encasement of the heart 36 or other organ upon which surgery is to be performed. This eliminates the necessity of complicated fastening devices and encircling shields as in the prior art. The rib structure or frame structure also provides effective means for holding the pad into the selected configuration encompassing or encircling the heart or other organ.

While the present invention has been illustrated and described by means of a single embodiment, it is to be understood that numerous changes and modifications may be made therein in the illustrated apparatus without departing from the spirit and scope of the invention as defined in the appended claims.

Having described my invention, I now claim:

1. An apparatus for inducing local temperature changes in a portion of the body comprising:
   a pad of a generally flat configuration constructed of a pliable material and having a heat transfer face and an insulating face, heat transfer means closely adjacent said heat transfer face for transferring heat between a heat conducting medium and said heat transfer face, insulating means disposed between said heat transfer means and said insulating face for insulating said insulating face from said heat transfer medium, and malleable means comprising a frame of malleable metal within said pad extending substantially throughout said body substantially parallel to said heat transfer face and being sufficiently deformable to be readily formed into selected shapes and being sufficiently resistant to deformation for retaining said pad in said selected shape.

2. The apparatus of claim 1, wherein said heat transfer means comprises a fluid conducting passage disposed in said body closely adjacent the heat transfer face.

3. The apparatus of claim 2, wherein said fluid conducting passage enters said pad at one end and exits at the other end and passes back and forth along a plurality of parallel lines between the sides thereof.

4. An apparatus for inducing local temperature changes in a portion of the body comprising:

a pad of a generally flat configuration constructed of a pliable material and having a heat transfer face and an insulating face, heat transfer means closely adjacent said heat transfer face for transferring heat between a heat conducting medium and said heat transfer face, insulating means comprising an air space disposed between said heat transfer means and said insulating face for insulating said face from said heat transfer medium, and malleable means within said pad for permitting said pad to be readily formed into selected shapes and for retaining said pad in said selected shape.

5. The apparatus of claim 4, wherein said material is a sterilizable plastic.

6. The apparatus of claim 1, wherein said frame comprises a central spine and a plurality of cross bars defining arms extending outward from said central body member.

7. The apparatus of claim 6, wherein said heat transfer means comprises a plurality of fluid conducting passages disposed in said body closely adjacent the heat transfer face.

8. An apparatus for inducing local temperature changes in a portion of the body comprising:

a pad of a generally flat configuration constructed of a pliable material and having a heat transfer face and an insulating face, heat transfer means closely adjacent said heat transfer face for transferring heat between a heat conducting medium and said heat transfer face, an air space disposed between said heat transfer means and said insulating face for insulating said insulating face from said heat transfer medium, and malleable means within said pad for a frame of malleable metal extending substantially through said body substantially parallel to said heat transfer face permitting said pad to be readily formed into selected shapes and for retaining said pad in said selected shape.

9. The apparatus of claim 8, wherein said material is a sterilizable elastomeric.

* * * * *